United States Patent [19]

Carl et al.

[11] 4,012,287

[45] Mar. 15, 1977

[54] METHOD AND REAGENT FOR THE QUANTITATIVE ANALYSIS OF TRIGLYCERIDES

[75] Inventors: Brigitte Carl; Jaroslav Stourac, both of Berlin, Germany

[73] Assignee: Dr. Bruno Lange GmbH, Berlin, Germany

[22] Filed: Nov. 18, 1975

[21] Appl. No.: 632,984

[52] U.S. Cl. .................... 195/103.5 R; 23/230 B; 252/408

[51] Int. Cl.² .................. G01N 33/16; G01N 31/14

[58] Field of Search ................. 23/230 B; 252/408; 195/103.5

[56] References Cited

UNITED STATES PATENTS

| | | | |
|---|---|---|---|
| 3,645,688 | 2/1972 | Smernoff | 23/230 B |
| 3,703,591 | 11/1972 | Bucolo et al. | 195/103.5 R |
| 3,791,791 | 2/1974 | Finkel | 23/230 B |
| 3,862,009 | 1/1975 | Wahlefeld | 195/103.5 R |
| 3,894,844 | 7/1975 | Pinto et al. | 23/230 B |
| 3,898,130 | 8/1975 | Komatsu | 195/103.5 R |

*Primary Examiner*—R.E. Serwin
*Attorney, Agent, or Firm*—Lane, Aitken, Dunner & Ziems

[57] ABSTRACT

A reagent and method for the quantitative of serum triglycerides which involves the alcoholic saponification of serum lipides using a low molecular weight chlorinated hydrocarbon as a catalyst. The saponified lipid is then mixed with an enzyme preparation for hydrolysis. After hydrolysis, the triglyceride is quantitatively analyzed in a conventional manner.

6 Claims, No Drawings

METHOD AND REAGENT FOR THE QUANTITATIVE ANALYSIS OF TRIGLYCERIDES

BACKGROUND OF THE INVENTION

In the field of prophylactic diagnosis it is important to have available a reliable analytical method for the quantitative analysis of triglycerides, i.e. one which provides reproduceable data.

An increase in the blood serum of the concentration of lipides, understood to include triglyderides, cholesterol derivatives and the phospholipides is seldom accompanied by clinical symptoms, nevertheless such increases are important risk factors associated with arteriosclerosis and the coronary diseases.

In contrast to the comparatively unspecific analysis for total lipides the quantitive analysis of the triglycerides and the cholesterol derivatives allows, in about 90 percent of cases, a specific diagnosis as to the type of the hyperlipidemy.

Such hyperlipidemies (also referred to as hyperlipoproteinemies since the fatty acid components or the lipides are rendered soluble in the aqueous transportation system of the human by bonding to proteins) can be diagnozed according to known prior methods by an analysis of the alcohol component, i.e. the glycerol of the fatty acid ester.

In order to analyze the fatty acid content it is necessary that the triglyceride be separated from the protein substrate and then saponified. These prior art methods give a quantitative value for fatty acids based on the quantitative analysis of the glycerol as formed by the saponification.

In the prior art methods the hydrolysis of the ester is effected either by ordinary alkaline hydrolysis, as in soap manufacture, which employs an alcoholic potassium hydroxide solution (a reesterification), or by enzyme hydrolysis using enzymes which specifically result in the hydrolysis of the ester bond.

In these methods the glycerol obtained by hydrolysis of the ester is reacted with adenosine triphosphate in the presence of glycerol-kinase to form glycerol-1-phosphate, and the adenosine triphosphate formed is reacted with phosphoenol pyruvate in the presence of a pyruvate-kinase to form pyruvate and adenosine triphosphate. The pyruvate is reduced with the hydrogenated form of nicotinamide adeninedi nucleotide to lactate. The resulting dehydrogenation of nicotinamide adeninedi nucleotide can be optically analyzed quantitatively since only the hydrogenated form has an absorption at 340 nm.

The triglyceride content is taken as the difference between the content of blood glycerides and blood glycerol.

The two prior art methods described above for the hydrolysis of lipides are attended by certain disadvantages. The alkaline saponification requires the use of an elevated temperature of about 55 to 70° C and a substantial time period, on the order of 20 to 30 minutes. Also the ester cleavage by means enzymes requires close regulation of the temperature to optimize the reaction velocity and to ensure the full efficiency of the enzymes. Thus enzyme hydrolysis, which requires maintaining the reaction medium precisely at a temperature of about 30° C, often poses difficulties to the ordinary practitioner, i.e. in the small laboratory of a practicing physician and performed by untrained personel. In this latter method, if the temperature is not properly maintained, the test inevitably results in erroneous data. Enzyme cleavage also requires a period of at least 10 minutes. An additional problem resides in the fact that the enzymes used for the hydrolysis show a decrease in activity (catalytic efficiency) upon storage, which introduces a further factor of uncertainty into the test. The enzymes are also comparatively expensive.

SUMMARY OF THE INVENTION

The present invention provides a method for the quantitative analysis of triglycerides in aqueous samples and involves the hydrolysis or cleavage of the lipide ester bond by means of saponification in the presence a specific catalyst to accelerate the hydrolytic cleavage. The method of the present invention requires only a few minutes and, in addition, eliminates temperature control as a critical factor. The catalyst used in the method of the present invention is a low molecular weight chlorinated hydrocarbon, preferably trichloromethane.

The advantages achieved by the invention include a shorter reaction time required for complete hydrolysis and its ability to be conducted at room temperature. By avoiding the ester cleavage of the prior art, the present method is rendered less expensive and more reliable.

Accordingly, it is an object of the present invention to provide a method for the quantitative analysis of lipides which is fast, reliable and inexpensive.

DESCRIPTION OF THE PREFERRED EMBODIMENTS

As indicated above, in the method of the present invention an enzyme capable of breaking the lipide ester bond, a low molecular weight chlorinated hydrocarbon catalyst and alkali are added to the lipide-containing serum sample to be analyzed. The enzymes suitable for use in the present invention include those conventionally used for the alkaline hydrolysis of lipides. The amount of enzyme used is conventional, and the invention is operable even with very small amounts of enzyme. Suitable catalysts include low molecular weight hydrocarbons such as methylene chloride, ethylene chloride, trichloromethane, etc. Trichloromethane is the preferred catalyst. The amount of catalyst used in the method of the present invention is not critical but will generally be in the range of 0.1 to 2.0 parts by weight per part by weight of aqueous test sample. A ratio of about 1:1 is preferred.

The hydrolysis reaction may conveniently be conducted at room temperature.

The test sample is rendered alkaline by conventional means, e.g. by the addition of a suitable amount of an alcoholic potassium hydroxide solution.

EXAMPLE

For purposes of comparison, triglycerides in a blood serum sample were analyzed both by alkaline hydrolysis of the serum in accordance with the present invention and by an enzymatic glycerol analysis in accordance with the conventional procedure.

Preparation of the Serum Sample:

Into a centrifuging tube is measured 0.5 ml of a 0.1 molar ethanolic potassium hydroxide solution and 0.1 ml serum and well mixed. Then 0.1 ml $CHCl_3$ is added and well mixed and left to stand at room temperature for 3 to 5 minutes.

Subsequently, 1.0 ml of 1.5 molar magnesium sulfate solution is added and the 1.7 ml mixture is centrifuged for about 5 minutes to produce a clear solution of saponified fatty acid ester.

Preparation of Enzyme Reagent:

Into a single use cuvette is introduced 1.7 ml of a buffer enzyme-coenzyme substrate solution containing the following components: 100 millimols triethanolamine HCl buffer (ph = 7.6), 1.32 millimols adenosine triphosphate (ATP), 0.43 millimols phosphoenol pyruvate (PEP), 0.54 millimols nicotinamide adenindinucleotide, reduced (NADH), about 7,700 units per liter lactate dehydrogenase (LDH), about 1,400 units per liter pyruvate kinase (PK). The contents of the cuvette are then lyophilized to produce the enzyme reagent.

Analysis:

The cuvette is opened and its contents are dissolved by the addition of 2.0 ml bidistilled water. 0.5 ml of the clear saponified solution is withdrawn and left at room temperature for about 10 minutes and the extinction $E_1$ is then measured. Another 1.0 ml of the clear saponified solution is mixed with the 2.0 ml of the enzyme solution and 0.02 ml of a glycero-kinase suspension is added. 0.77 units per liter of glycero-kinase (GK), in the form of an ammonium sulfate suspension, is required to initiate the reaction. The mixture of enzymes and saponified serum esters is allowed to sit for 10 minutes. Then the extinction $E_2$ is measured the extinction difference ($\Delta E = E_1 - E_2$) is calculated and used in the calculation for triglyceride.

In connection with each analysis or series of analyses a value for a blank test must be obtained wherein, instead of 0.1 ml serum, there is measured 0.1 ml bidistilled water into the centrifuging tube. The remainder of the procedure for the blank analysis is identical to the actual analytical procedure. The extinction difference of the blank analysis ($\Delta E_1$) is deducted from the extinction difference of the analytical data ($\Delta E_a$). $\Delta E_a - \Delta E_1 = \Delta E_{CORRECTED}$ The calculation is made according to the equation:

$$\text{mg triglycerides per 100 ml} = F \cdot \Delta E_{CORRECTED}$$

wherein F is the extinction coefficient.

With routine analyses it is recommended to deduct the 10 mg/100 ml from the calculated triglyceride value as a correction for the free glycerol;

$$\text{mg triglyceride/100 ml} - 10 \text{ mg/100 ml} = \text{mg triglyceride/100 ml}_{CORRECTED}$$

Table

Triglyceride content of human serum samples (mg/100 ml)

| Patient | lipide hydrolysis with alcoholic KOH (20–30 minutes 55–70° C) | lipide hydrolysis with alcoholic KOH+CHCl₃ (3 min. room temp.) |
| --- | --- | --- |
| 1 | 121 | 138 |
| 2 | 159 | 176 |
| 3 | 104 | 111 |
| 4 | 162 | 162 |
| 5 | 99 | 100 |
| 6 | 67 | 69 |
| 7 | 125 | 112 |
| 8 | 190 | 161 |
| 9 | 242 | 225 |
| 10 | 91 | 101 |
| 11 | 389 | 380 |
| 12 | 97 | 103 |
| 13 | 189 | 203 |
| 14 | 164 | 171 |
| 15 | 108 | 108 |
| 16 | 132 | 138 |
| 17 | 83 | 95 |
| 18 | 80 | 79 |
| 19 | 113 | 97 |
| 20 | 165 | 156 |
| 21 | 45 | 50 |
| 22 | 257 | 257 |
| 23 | 184 | 179 |
| 24 | 231 | 236 |
| 25 | 127 | 126 |
| 26 | 76 | 78 |
| 27 | 152 | 160 |
| 28 | 73 | 74 |
| 29 | 101 | 107 |
| 30 | 138 | 140 |
| 31 | 146 | 134 |
| 32 | 137 | 143 |
| 33 | 182 | 177 |
| 34 | 154 | 147 |
| 35 | 213 | 195 |
| 36 | 155 | 166 |
| 37 | 131 | 136 |
| 38 | 443 | 459 |
| 39 | 428 | 435 |
| 40 | 102 | 98 |
| 41 | 153 | 161 |

We claim:

1. A reagent for the quantitative analysis of triglycerides comprising: an alcoholic solution of potassium hydroxide, an aqueous solution of magnesium sulfate, and a low molecular weight chlorinated hydrocarbon.

2. The reagent of claim 1 wherein said chlorinated hydrocarbon is trichloromethane.

3. The reagent of claim 2 wherein said trichloromethane constitutes about 17% by weight of said reagent.

4. In a method for the quantitative analysis of triglycerides by enzyme hydrolysis of said triglyceride in an alkaline aqueous medium to form glycerol, followed by quantitative analysis of the glycerol, the improvement which consists of adding a catalytic amount of a low molecular weight chlorinated hydrocarbon to the hydrolysis medium to accelerate the hydrolytic cleavage.

5. The method of claim 4 wherein said low molecular weight chlorinated hydrocarbon is trichloromethane.

6. The method of claim 4 wherein said trichloromethane is added in an amount of about 20% by weight, based on the amount of the alkaline hydrolysis medium.

* * * * *